United States Patent [19]
Yang et al.

[11] Patent Number: 5,399,344
[45] Date of Patent: Mar. 21, 1995

[54] SYNERGISTIC FLY ATTRACTANT COMPOSITION

[75] Inventors: Kim W. Yang, Dallas; David R. Kinzer, Argyle; Ronald B. Winslow, Dallas, all of Tex.

[73] Assignee: Sandoz Ltd., Basel, Switzerland

[21] Appl. No.: 870,440

[22] Filed: Apr. 16, 1992

[51] Int. Cl.⁶ ..................... A01N 25/02; A01N 33/04
[52] U.S. Cl. ..................... 424/84; 424/405; 514/557; 514/663
[58] Field of Search ............... 424/405, 84; 574/557, 574/558, 663

[56] References Cited

U.S. PATENT DOCUMENTS

| | | | |
|---|---|---|---|
| 2,307,775 | 1/1943 | Flennes et al. | 167/37 |
| 3,996,349 | 12/1976 | Mulla et al. | 424/84 |
| 4,855,133 | 8/1989 | Kamei et al. | 424/84 |
| 5,008,107 | 4/1991 | Warner | 424/84 |

FOREIGN PATENT DOCUMENTS 229191  7/1986  European Pat. Off. ..... A01N 27/00

OTHER PUBLICATIONS

Mulla, Chem. Abstracts, vol. 89, No. 25, 210362h Jun. 19, 1989.
J. Econ. Ent. vol. 70 No. 5 p. 644 ff (1977) Mulla et al.
J. Chem. Ecol. vol. 10 No. 2 p. 349 ff (1984) Mulla et al.

*Primary Examiner*—Gollamudi S. Kishore
*Assistant Examiner*—Neil Levy
*Attorney, Agent, or Firm*—Lynn Marcus-Wyner; Allen E. Norris

[57] ABSTRACT

Method for the preparation of an insect attractant composition which includes a trialkylamine salt, an alkali salt of a carboxylic acid and a pheromone in a suitable aqueous solution.

10 Claims, No Drawings

SYNERGISTIC FLY ATTRACTANT COMPOSITION

FIELD OF THE INVENTION

This invention concerns the preparation of a composition comprising a trialkylamine salt and a carboxylic acid alkali salt which when dissolved in an appropriate aqueous solution produces a fly attractant composition. The attractancy activity of the binary mixture of a trialkylamine salt and a carboxylic acid alkali salt can be increased by the addition of an appropriate pheromone which may result in a synergistic attractant composition. Methods of using the subject compositions include delivery of the separate components, either as solids or formulated in an appropriate solvent, to an appropriate aqueous solution or formulation of the separate components into binary or trinary mixtures and sealing in for example ampoules, water soluble packages or pouches, tablets, pellets, incorporation into soluble polymers or other general methods of encapsulation.

DESCRIPTION OF RELATED ART

Mulla et al, *J. Economic Entomology*, 1977, 70,644 reported a synthetic fly attractant (SFA) composition composed of trimethylamine hydrochloride, ammonium chloride, indole and linoleic acid formulated as a solid on fishmeal. The SFA composition proved to be more effective as a fly attractant than the individual components tested separately or than sugar-bait formulations of the fly pheromone cis-9-tricosene, here after referred to as muscalure. While addition of various carboxylic acids enhanced the general fly attractancy activity of the SFA, the observed activity enhancement with n-butyric acid was not significant compared to SFA formulations without the acid.

Mulla et al, *J. Chem. Ecology*, 1984, 10,439 has also reported that the combination of trimethylamine hydrochloride and n-butyric acid in an inert anchovy meal formulation did significantly improve fly attractant efficacy over trimethylamine hydrochloride formulations without n-butyric acid.

Warner, U.S. Pat. No. 5,008,107 discloses a fly attractant composition composed of indole or skatole, t-he pheromone muscalure and trimethylamine hydrochloride incorporated in a suitable carrier. The pheromone was included in the synthetic fly attractant composed of trimethylamine hydrochloride and indole or skatole to serve as a sex attractant in order to act to remove a proportionally greater number of females than males so as to significantly impact succeeding fly generations.

DESCRIPTION OF THE INVENTION

The present invention provides a method for the preparation of a composition for the attraction of insects which utilizes various components known to possess fly attractant properties but as the result of changes in the physical properties of some of the components as well as a synergistic effect between others results in a greater attractive effect than the individual components alone. The present invention also provides a means for producing a stable, non-odorous formulation of the components, either individually or in combination, which upon mixing with an aqueous solution produces the insect attractancy effect.

Aqueous solutions are solutions made from, with or by water. For example, appropriate aqueous solutions include water or an organic solvent which can be mixed with water so that the weight percent of water in the solution is equal to or greater than five percent. Organic solvents include, but are not limited to, alcohols, such as methanol, ethanol or propanol. While in its preferred embodiment the organic solvent forms a homogenous solution with water, the aqueous solution may also be heterogenous where the organic solvent and water are not directly miscible.

The present invention pertains to an attractant composition produced when a trialkylamine salt is combined with an alkali salt of a carboxylic acid in the presence of water. Addition of a pheromone to this attractant composition results in a further composition whose attractancy activity is greater than found for the original attractant composition or the pheromone separately. Where the pheromone added to the attractant composition of a trialkylamine salt and a carboxylic acid alkali salt is muscalure, the attractant composition is a highly efficacious agent for the attraction of synanthropic flies to a specific location, such as a trap or toxic bait.

The first ingredient is a trialkylamine salt where the alkyl groups are selected from methyl or ethyl. Of the trialkylamines known to serve as fly attractants, trimethylamine is preferred, but due to its gaseous nature, an inorganic salt of trimethylamine is used. While numerous salts of trialkylamines are known, including hydrohalides and hydrosulfates, the trialkylamine salt most commonly employed is trimethylamine hydrochloride. Upon contact with water, the trimethylamine salt readily dissociates and releases trimethylamine which in turn stimulates a favorable olfactory response in flies. The use of trimethylamine hydrochloride as the constituent to provide the trimethylamine gas is an attractive composition as it has a considerably less noxious odor to humans until the dissociation in the presence of water takes place. The concentration of this component is determined by the unit of measure and the volume of appropriate aqueous solution into which the unit is to be added.

The second ingredient is an alkali salt of a $C_2$ to $C_{18}$ linear or branched and saturated or unsaturated carboxylic acid. While various free carboxylic acids are known to be attractive to flies (Mulla, 1984), those of lower molecular weight are not readily utilized as components of attractant compositions due to their strong, unpleasant odor to humans (Mulla, 1977). However, the use of alkali salts of carboxylic acids offers an advantage over the corresponding free carboxylic acids in that the corresponding alkali salts are 1) non-volatile thus eliminating unpleasant odors which are characteristic of the lower molecular weight acids (e.g. $C_3$ to $C_8$) until activated by water; 2) less corrosive than the corresponding free acid and thus 3) easier and safer to handle. While various alkali salts including lithium, sodium and potassium of various $C_2$ to $C_{18}$ carboxylic acids, such as acetic, n-butyric, iso-butyric and linoleic acid are known, the preferable carboxylic acid alkali salt is sodium n-butyrate. The concentration of this component is determined by the unit of measure and the volume of appropriate aqueous solution into which the unit is to be added.

The use of the binary mixture of a trialkylamine salt and an alkali salt of a carboxylic acid allows for the slow release of insect attractant when combined in the presence of water. In an aqueous solution, the trialkylamine salt and the alkali salt of the carboxylic acid form a stable intermediate salt which then slowly dissociates releasing the attractant substances, trimethylamine and the carboxylic acid.

A possible third constituent is a pheromone, selected for its ability to attract a desired species of insect. Pheromones are chemical substances produced by animals which serve as a stimulus to other individuals of the same species for one or more behavioral responses including but not limited to sex, food, aggregation or oviposition lures. A sex pheromone is broadly defined as a substance released by one member of a species to attract the opposite member for the purpose of mating. A large number of pheromones have been disclosed in U.S. Pat. No. 5,046,280, the contents of which in this respect are incorporated herein by reference. Where in the present invention it is desired to attract flies, the pheromone of choice is muscalure. Muscalure is produced by the female fly and can serve both as an aggregative and sex attractant.

The fly attractant compositions according to the present invention may be used in mechanical as well as non-mechanical traps including sticky traps. They may also be used with a toxicant or toxic bait to which the fly is lured by the fly attractant. The components, either individually or as mixtures, can be delivered in pure solid form or incorporated in an appropriate carrier; formulated with appropriate organic solvents and delivered as a solution; sealed in ampoules or water soluble packets or pouches; formulated into tablets, pellets or gels; incorporated into soluble polymers; encapsulated or other appropriate forms of delivery.

The preferred embodiments of the present invention are as disclosed in the claims, combinations thereof being particularly preferred; the most preferred being sodium n-butyrate, trimethylamine hydrochloride and muscalure.

The attractancy capability of a trinary mixture prepared from a trialkylamine salt, a carboxylic acid alkali salt and a pheromone has been found to be significantly greater than that found for the binary attractant combination of the trialkylamine salt and carboxylic acid alkali salt or the individual pheromone alone. The synergism between the trialkylamine salt, the carboxylic alkali salt and the pheromone results in a composition with enhanced attractancy. The following examples illustrate various embodiments of the present invention and are not intended as a limitation of the scope thereof:

EXAMPLE I

Biological efficacy tests were conducted on commercial cattle feed lots in Melissa, Tex. with all test materials exposed to the naturally occurring house fly populations.

The test method utilized addition of the synergistic attractant composition to Fly Terminator Traps, sold by Farnam Companies, Inc. of Phoenix, Ariz., a non-insecticidal containing trap consisting of a wide mouth one gallon plastic jar filled with one-half gallon of water and fitted with a screw-on cover device. The cover device, approximately 4" high, consisted of a hanger, a domed cover, and a baffle with openings to the jar to allow the attractant to escape and the flies to enter. Upon entering the jar through the cover, the flies were unable to escape and eventually drowned in the water solution.

The traps were suspended in the shade at one to two feet above the base of feed bunks which provided an environment for large numbers of flies. Examples of synanthropic flies attracted to the traps included house fly, lesser house fly, blow fly, flesh flies and eye gnats.

The attractant candidate test materials were individually measured into separate water soluble polyvinylacetate (PVA) packets and sealed. Individual packets contained 0.065 g of muscalure formulated on sugar; 3.30 g of sodium n-butyrate and 2.87 g of trimethylamine hydrochloride.

| Combination | A. muscalure |
| --- | --- |
| | B. sodium n-butyrate trimethylamine hydrochloride |
| | C. sodium n-butyrate trimethylamine hydrochloride muscalure |

TEST 1

A single packet of each individual component, in accordance with the test combination, was added to 1.89 liters of water in the test container and the number of dead flies determined after the indicated time:

| | Mean Fly Count | | | | | |
| --- | --- | --- | --- | --- | --- | --- |
| Combination/Time (hr) | 0.25 | 0.58 | 2.25 | 24 | 48 | 144 |
| A | 0 | 0 | 7 | 25 | 200 | 1500 |
| B | 2 | 14 | 45 | 50 | 100 | 2000 |
| C | 8 | 15 | 90 | 500 | 1500 | 4500 |

The data demonstrates that a synergistic relationship exists for the trinary combination of trimethylamine hydrochloride, sodium n-butyrate and muscalure. At one day (24 hours), combination C was 20 times more effective than muscalure alone and 10 times more effective than the binary combination B. After 2 days (48 hours), the fly attractant activity of combination C was 8 times greater than muscalure alone and 15 times greater than binary combination B.

TEST 2

Multiple packets of the individual components representative of combination C were added to 1.89 liters of water in test containers to produce final aqueous concentrations (weight percent) of the individual components of C1: 0.17% sodium n-butyrate, 0.15% trimethylaminehydrochloride and 0.0033% muscalure; C2: 0.34% sodium n-butyrate, 0.30% trimethylamine hydrochloride and 0.0066% muscalure; C3: 0.51% sodium n-butyrate, 0.46% trimethylamine hydrochloride and 0.01% muscalure. The standard was Farnam Fly Attractant (Farnam Companies, Phoenix, Ariz) and was used according to label directions.

| Concentration/Time | Mean Fly Count | | | | | |
| --- | --- | --- | --- | --- | --- | --- |
| (days) | 1 | 2 | 3 | 7 | 10 | 14 |
| C1 | 500 | 750 | 750 | 3000 | 4000 | 4000 |
| C2 | 700 | 1000 | 1000 | 3500 | 4000 | 4500 |
| C3 | 500 | 750 | 750 | 3500 | 4000 | 4750 |
| Farnam Fly Attractant | 400 | 400 | 400 | 2000 | 2500 | 3000 |

As noted from the data, after two days the synergistic fly attractant composition C attracted an average of 2.1 times as many flies for all three concentrations studied (C1, C2 and C3) as were attracted with the standard Farnam Fly Attractant. After ten days, the synergistic fly attractant composition C attracted an average of 1.6 time as many flies for all three concentrations studied (C1, C2, C3) compared with the standard. After 14 days, the synergistic fly attractant composition C attracted an average of 1.5 times as many flies for all three concentrations examined (C1, C2, C3) compared to the standard.

The surprising aspect of the use of the various concentrations of composition C was that over the wide dose ranges examined, composition C proved more effective at all concentrations with regards to the number of flies attracted than the commercial standard.

The components of the present invention may be delivered as a unit measure of each individual component as pure compound from a bulk reservoir; or a unit measure of packets soluble in aqueous solution which individually contain pure or formulated compound; or a unit measure of packets soluble in aqueous solution where each packet contains a given measure of the components formulated together; or a unit measure of formulated tablets, pellets or gels which individually contain pure compound; or a unit measure of formulated tablets, pellets or gels which contain a given measure of the components formulated together; or a unit measure of a soluble polymer containing a measure of pure compound; or a soluble polymer containing a measure of the components formulated together; or a unit measure of pure or formulated components in an ampoule; or a unit of measure of pure or combined components which have been encapsulated.

The synergistic fly attractant composition of the present invention may be used in conjunction with mechanical or non-mechanical traps, electrocutors, scatter bait or in conjunction with one or more insecticidal agents. Such insecticidal agents include, but are not limited to: organophosphates such as bomyl, dimethyl 3-hydroxy glutaconate dimethyl phosphate or dichlorvos, 2,2-dichlorovinyl dimethyl phosphate or methomyl, S-methyl-N-((methylcarbamoyl)oxy)-thioacetimidate; carbamates such as propoxur, 2-(1-methylethoxy)phenyl methylcarbamate or carbofuran, 2,3-dihydro-2,2-dimethyl-7-benzofuranyl methylcarbamate; nitromethylene heterocycles such as tetrahydro-2-(nitromethylene)-2H-1,3-triazine or other analogs such as disclosed in U.S. Pat. Nos. 3,993,648 and 4,065,560; insect growth regulators such as methoprene, isopropyl (2E, 4E)-11-methoxy-3,7,11-trimethyl-2-4-dodecadienoateorhydroprene, ethyl (2E, 4E)-3,7,11-trimethyldodeca-2,4-dienoate; and biological insecticides such as *Bacillus thuringiensis var. kurstaki* or *B.t. var. israelensis*. The percentage of weight of insecticide added to the attractant composition for the desirable results is determined in part by the toxicity of the insecticide selected and is generally within the range of 0.05%.to 15% by weight of the final solution.

The synergistic fly attractant composition of the present invention may be used in conjunction with non-insecticidal mechanical bait traps as descibed in U.S. Pat. Nos. 4,908,977 and 5,046,280, the contents of which in this respect are incorporated herein by reference, as well as sticky traps and Fly Snippers.

The fly attractant composition of the present invention may be used in conjunction with scatter bait including Golden Malrin and Improved Golden Malrin (Zoecon Corp., Dallas, Tex.). The components of the fly attractant composition can be brought together in an appropriate aqueous solution and poured either directly on the general area in which the scatter bait is placed or in to a container, which would allow for dispersion of the evolved attractant gases, near the area of the scattered bait.

Additionally, dispersing agents, emulsifiers, surfactants, theology controlling agents, such as xanthin gum or alcohol, preservatives, conditioners, and the like maybe variously employed in combination with the present invention without departing from the scope of the invention claimed.

What is claimed is:

1. A method of preparing an insect attractant composition comprising mixing in an aqueous solution an insect attractant effective aggregate amount consisting essentially of:
    (a) a trialkylamine salt where the alkyl groups are selected from methyl or ethyl; and
    (b) an alkali salt of a $C_2$ to $C_{18}$, linear or branched and saturated or unsaturated carboxylic acid.
2. A method according to claim 1 wherein component (a) is trimethylamine hydrochloride.
3. A method according to claim 1 where component (b) is sodium n-butyrate.
4. A method according to claim 1 where the concentration of component (a) is 0.02 to 1.0 weight percent in the aqueous solution.
5. A method according to claim 1 where the concentration of component (b) is 0.02 to 1.0 weight percent in the aqueous solution.
6. A method according to claim 1 comprising the additional step of mixing in an attractant effective amount of a pheromone.
7. The method according to claim 1 comprising the further step of adding an insecticidally effective amount of an insecticide.
8. A method according to claim 6 where the pheromone is muscalure.
9. A method according to claim 6 where the concentration of the pheromone is 0.001 to 0.1 weight percent.
10. The method according to claim 6 comprising the further step of adding an insecticidally effective amount of an insecticide.

* * * * *